US012698256B2

(12) United States Patent
Zenasni et al.

(10) Patent No.: US 12,698,256 B2
(45) Date of Patent: Aug. 4, 2026

(54) HYDROCARBON FUNCTIONALIZED POLYAMINES FOR CORROSION INHIBITION

(71) Applicant: Ecolab USA Inc., St. Paul, MN (US)

(72) Inventors: Oussama Zenasni, Houston, TX (US); John Nathan Scholz, Sugar Land, TX (US); Philip Andrew Thornthwaite, Wigan (GB); Maria DeJesus Marquez, Houston, TX (US); Ana Ferrer Carrera, Missouri City, TX (US); Ashish Dhawan, Aurora, IL (US)

(73) Assignee: Ecolab USA Inc., St. Paul, MN (US)

( * ) Notice: Subject to any disclaimer, the term of this patent is extended or adjusted under 35 U.S.C. 154(b) by 957 days.

(21) Appl. No.: 17/817,878

(22) Filed: Aug. 5, 2022

(65) Prior Publication Data

US 2023/0042309 A1 Feb. 9, 2023

Related U.S. Application Data

(60) Provisional application No. 63/203,960, filed on Aug. 5, 2021.

(51) Int. Cl.

*C07C 237/10* (2006.01)
*C07C 211/14* (2006.01)
(Continued)

(52) U.S. Cl.

CPC .......... *C07C 237/10* (2013.01); *C07C 211/14* (2013.01); *C09K 15/18* (2013.01);
(Continued)

(58) Field of Classification Search

CPC ..... C07C 237/10; C07C 211/14; C09K 15/18; C09K 15/22; C23F 11/141; C23F 11/145
See application file for complete search history.

(56) References Cited

U.S. PATENT DOCUMENTS 2,598,213 A 5/1952 Blair, Jr.
3,247,094 A 4/1966 Dajani
(Continued)

FOREIGN PATENT DOCUMENTS

CN 104673471 A 6/2015
EP 0 526 251 A1 2/1993
(Continued)

OTHER PUBLICATIONS

Carbohydr. Polym. 2017, 156, 202-214 (Mobin et al.) (Year: 2017).*
(Continued)

*Primary Examiner* — Amy C Bonaparte
*Assistant Examiner* — Derek Rhoades
(74) *Attorney, Agent, or Firm* — Stinson LLP

(57) ABSTRACT

Compositions and methods are provided for reducing, inhibiting, or preventing corrosion of a surface, the polyamine compounds corresponding to the structure of Formula 1 or 2, or a salt thereof:

(1)

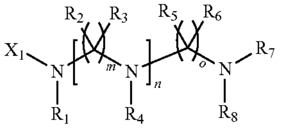

wherein $X_1$ is —C(O)$R_9$ or —$[C(R_{10}R_{11})]_p$—$C(R_{12})(X_2)$—$R_{13}$; $X_2$ is —OH or —$NH_2$; $R_1$ and $R_4$ are independently hydrogen, alkyl, or —$[C(R_{10}R_{11})]_p$—$C(R_{12})(X_2)$—$R_{13}$; $R_2$, $R_3$, $R_5$, $R_6$, $R_7$, $R_8$, $R_{10}$, $R_{11}$, and $R_{12}$ are independently hydrogen or alkyl; $R_9$ and $R_{13}$ are independently $C_7$ to $C_{30}$ alkyl or alkenyl; m and o are integers from 1 to 10; n is an integer from 1 to 6; and p is an integer from 1 to 10;
(Continued)

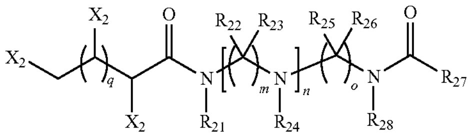

(2)

wherein $X_2$ is —OH or —$NH_2$; $R_{21}$, $R_{22}$, $R_{23}$, $R_{24}$, $R_{25}$, $R_{26}$, and $R_{28}$ are independently hydrogen or alkyl; $R_{27}$ is $C_{10}$ to $C_{30}$ alkyl or alkenyl; m and o are integers from 1 to 10; n is an integer from 1 to 6; and q is an integer from 0 to 10.

17 Claims, 4 Drawing Sheets

(51) Int. Cl.

| | |
|---|---|
| ***C09K 15/18*** | (2006.01) |
| ***C09K 15/22*** | (2006.01) |
| ***C23F 11/14*** | (2006.01) |

(52) U.S. Cl.

CPC ............ *C09K 15/22* (2013.01); *C23F 11/141* (2013.01); *C23F 11/145* (2013.01)

(56) References Cited

U.S. PATENT DOCUMENTS

| | | | |
|---|---|---|---|
| 3,458,453 | A | 7/1969 | Kautsky |
| 3,819,328 | A | 6/1974 | Go |
| 4,344,861 | A | 8/1982 | Levy |
| 4,842,716 | A | 6/1989 | Kaplan et al. |
| 5,151,220 | A | 9/1992 | Majestic et al. |
| 5,174,957 | A | 12/1992 | McCullough |
| 5,322,630 | A | 6/1994 | Williams et al. |
| 5,415,805 | A | 5/1995 | Brown et al. |
| 5,427,999 | A | 6/1995 | Clewlow et al. |
| 5,851,377 | A | 12/1998 | Bush |
| 5,853,619 | A | 12/1998 | Watson et al. |
| 6,063,334 | A | 5/2000 | Naraghi |
| 6,548,016 | B1 | 4/2003 | Borgard |
| 9,290,584 | B2 | 3/2016 | Ng et al. |
| 9,382,467 | B2 | 7/2016 | Meyer et al. |
| 9,434,911 | B2 | 9/2016 | Bennett et al. |
| 9,534,300 | B2 | 1/2017 | Gill et al. |
| 10,604,710 | B2 | 3/2020 | Moloney |
| 2013/0302210 | A1 | 11/2013 | Patel et al. |
| 2014/0034003 | A1 | 2/2014 | Corradi et al. |
| 2014/0128294 | A1 | 5/2014 | Gatlin et al. |
| 2016/0114338 | A1 | 4/2016 | Snead |
| 2017/0342310 | A1 | 11/2017 | Obeyesekere et al. |
| 2018/0244605 | A1 | 8/2018 | Khanlari et al. |
| 2019/0062187 | A1 | 2/2019 | Dhawan et al. |
| 2019/0203131 | A1 | 7/2019 | Yu et al. |

FOREIGN PATENT DOCUMENTS

| | | | |
|---|---|---|---|
| EP | 0 593 294 | A1 | 4/1994 |
| EP | 1 043 423 | A2 | 10/2000 |
| GB | 866408 | | 4/1961 |
| GB | 1410788 | | 10/1975 |
| WO | 2014/178737 | A1 | 11/2014 |
| WO | 2019/066911 | A1 | 4/2019 |
| WO | 2020/046967 | A1 | 3/2020 |

OTHER PUBLICATIONS

Ind. Eng. Chem. Res. 2019, 58, 17918-17927 (Patil et al.) (Year: 2019).*

International Search Report and Written Opinion dated Oct. 31, 2022 relating to PCT/US2022/039530, 11 pages.

International Search Report and Written Opinion dated Nov. 4, 2022 relating to PCT/US2022/039542, 14 pages.

* cited by examiner

HYDROCARBON FUNCTIONALIZED POLYAMINES FOR CORROSION INHIBITION

CROSS REFERENCE TO RELATED APPLICATIONS

This application claims priority to U.S. Provisional Patent Application Ser. No. 63/203,960 filed on Aug. 5, 2021, the disclosure of which is incorporated herein by reference in its entirety.

STATEMENT REGARDING FEDERALLY SPONSORED RESEARCH OR DEVELOPMENT

Not applicable.

THE NAMES OF PARTIES TO A JOINT RESEARCH AGREEMENT

Not applicable.

REFERENCE TO A SEQUENCE LISTING, TABLE, OR COMPUTER PROGRAM LISTING APPENDIX SUBMITTED ON A COMPACT DISC AND AN INCORPORATION-BY-REFERENCE OF THE MATERIAL ON A COMPACT DISC

Not applicable.

FIELD OF THE INVENTION

Compounds, compositions and methods are provided for reducing, inhibiting, or preventing corrosion of a surface, using substituted polyamine compounds. The polyamine compound has a structure corresponding to Formula 1 or 2, or a salt thereof.

BACKGROUND OF THE INVENTION

Corrosion of metal surfaces in aqueous media has long been a problem for industries such as the oil and gas industry, food/beverage industry, wash/sanitizing industry, pulp and paper, power generation, manufacturing, and utilities. For example, it is well known that during the production and refining of oil and gas several other corrosive components are present such as brines, organic acids, carbon dioxide, hydrogen sulfide, and microorganisms. These aggressive constituents can cause severe corrosion as evidenced by surface pitting, embrittlement, and general loss of metal. The metallic surfaces can be composed of high alloy steels including chrome steels, ferritic alloy steels, austenitic stainless steels, precipitation-hardened stainless steels, and high nickel content steels, copper, and carbon steels.

There are several mechanisms responsible for corrosion of metals. In corrosive water systems, the overall corrosion rate is controlled by the reduction of oxygen inhibiting the cathodic reaction. However, the most robust and cost-effective water treatment programs include both anodic and cathodic inhibitors to block reactions at both the anode and the cathode.

Corrosion inhibitors are usually surface-active compounds that form protective coatings on the surface of metals and suppress corrosion by preventing or reducing contact of the corrosive species to the pipeline surface. Common corrosion inhibitors are composed of amines, condensation products of fatty acids with polyamines, imidazolines, and/or quaternary ammonium compounds. Among the most frequently used corrosion inhibitors in crude oil and natural gas extraction are imidazoline derivatives and benzyldimethylalkylammonium chlorides.

Many regions around the world are extremely conscious about the potential harmful effects of chemical use in environmentally sensitive areas. Components in such products are often evaluated for their potential to bioaccumulate in organisms, their ability to biodegrade, and their toxicity in select aquatic species. The combination of these tests allows the regional authorities to assess the potential danger to the area of interest and permit or deny the use of the chemical.

Many corrosion inhibitor formulations have components that are toxic, bioaccumulate, or have biodegradation profiles that are not advantageous for the environment. As such, the development of new, high-performance actives that meet the stringent environmental regulations of these regions is needed.

BRIEF SUMMARY OF THE INVENTION

Disclosed herein are polyamine compounds and their use in methods for inhibiting corrosion at a surface, the polyamine compounds corresponding to the structure of Formula 1 or 2, or a salt thereof:

(1)

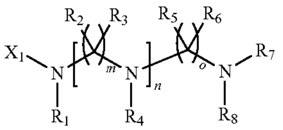

wherein $X_1$ is —C(O)$R_9$ or —$[C(R_{10}R_{11})]_p$—$C(R_{12})(X_2)$—$R_{13}$; $X_2$ is —OH or —$NH_2$; $R_1$ and $R_4$ are independently hydrogen, alkyl, or —$[C(R_{10}R_{11})]_p$—$C(R_{12})(X_2)$—$R_{13}$; $R_2$, $R_3$, $R_5$, $R_6$, $R_7$, $R_8$, $R_{10}$, $R_{11}$, and $R_{12}$ are independently hydrogen or alkyl; $R_9$ and $R_{13}$ are independently $C_7$ to $C_{30}$ alkyl or alkenyl; m and o are integers from 1 to 10; n is an integer from 1 to 6; and p is an integer from 1 to 10;

(2)

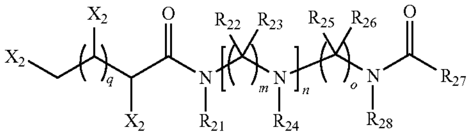

wherein $X_2$ is —OH or —$NH_2$; $R_{21}$, $R_{22}$, $R_{23}$, $R_{24}$, $R_{25}$, $R_{26}$, and $R_{28}$ are independently hydrogen or alkyl; $R_{27}$ is $C_{10}$ to $C_{30}$ alkyl or alkenyl; m and o are integers from 1 to 10; n is an integer from 1 to 6; and q is an integer from 0 to 10.

For the methods described herein, the polyamine compound has a structure of Formula 1.

For the methods, the polyamine compound of Formula 1 has $X_1$ of —C(O)$R_9$.

Alternatively, the polyamine compound of Formula 1 has $X_1$ of —$[C(R_{10}R_{11})]_p$—$C(R_{12})(X_2)$—$R_{13}$.

Additionally, the polyamine compound of Formula 1 has $R_2$, $R_3$, $R_5$, $R_6$, $R_7$, $R_8$, $R_{10}$, $R_{11}$, and $R_{12}$ are independently hydrogen, methyl, or ethyl; preferably, $R_2$, $R_3$, $R_5$, $R_6$, $R_7$, $R_8$, $R_{10}$, $R_{11}$, and $R_{12}$ are hydrogen.

The polyamine compound of Formula 1 can have $R_1$ and $R_4$ independently be hydrogen or —[C($R_{10}R_{11}$)]$_p$—C($R_{12}$)($X_2$)—$R_{13}$.

Additionally, the polyamines of Formula 1 can have $R_9$ and $R_{13}$ independently be $C_7$ to $C_{20}$ alkyl or alkenyl; $C_{11}$ to $C_{18}$ alkyl or alkenyl; or $C_{11}$ to $C_{14}$ alkyl or alkenyl.

For the methods described herein, the polyamine compounds of Formula 1 have $X_2$ of —OH.

For the polyamine compounds of Formula 1, m is an integer from 2 to 6; preferably, m is an integer from 2 to 3; more preferably, m is an integer of 2.

For the polyamine compounds of Formula 1, n is an integer from 2 to 6; preferably, n is an integer from 2 to 4; more preferably, n is an integer of 2 or 3.

The polyamine compounds of Formula 1 also have o as an integer from 2 to 6; preferably, o is an integer from 2 to 3; more preferably, o is an integer of 2.

For the polyamine compounds of Formula 1, p is an integer from 1 to 4; preferably, p is an integer of 1.

For the methods disclosed herein, the polyamine compound has a structure of Formula 2.

For the polyamine compounds of Formula 2, $X_2$ is —OH.

The polyamine compounds of Formula 2 have $R_{21}$, $R_{22}$, $R_{23}$, $R_{24}$, $R_{25}$, $R_{26}$, and $R_{28}$ of independently hydrogen, methyl, or ethyl.

The polyamine compounds of Formula 2 have m of an integer from 2 to 6; preferably, m of an integer of 2 or 3; more preferably, m of an integer of 2.

The polyamine compounds of Formula 2 have n of an integer from 2 to 6; preferably, n of an integer from 2 to 4; more preferably, n of an integer of 2 or 3.

The polyamine compounds of Formula 2 have o of an integer from 2 to 6; preferably, o of an integer of 2 or 3; more preferably, o of an integer of 2.

The polyamine compounds of Formula 2 also have q of an integer from 0 to 6; preferably, q of an integer from 1 to 4; more preferably; q of an integer of 1 or 2; most preferably, q is 0.

For the methods of corrosion inhibition described herein, the polyamine compound of formula 1 or 2 is added to a fluid that contacts the surface.

In these corrosion inhibition methods, the surface is a metal surface.

In the corrosion inhibition methods described herein, the surface is part of a piece of equipment in an oil and gas refinery.

In the methods described, the piece of equipment is in a unit susceptible to aqueous corrosion in a refinery or petrochemical plant. Particularly, the piece of equipment is an amine unit, a crude distillation unit, or a fluid catalytic cracking unit.

The polyamine compound of Formula 1 or 2 forms a film on the surface.

Further, the polyamine compound of Formula 1 or 2 passivates the surface.

In the corrosion inhibition methods disclosed, the polyamine compound of Formula 1 or 2 is contacted with the surface at a concentration from 1 ppm to 1000 ppm based on the weight of vapor or liquid contacting the surface; preferably, the polyamine compound of Formula 1 or 2 is contacted with the surface at a concentration from 5 ppm to 500 ppm; more preferably, the polyamine compound of Formula 1 or 2 is contacted with the surface at a concentration from 5 ppm to 250 ppm; even more preferably, the polyamine compound of Formula 1 is contacted with the surface at a concentration from 5 ppm to 100 ppm.

Other objects and features will be in part apparent and in part pointed out hereinafter.

BRIEF DESCRIPTION OF THE SEVERAL VIEWS OF THE DRAWING

FIG. 1(*b*) is a bar graph depicting % protection of proposed invention 1 and comparative compounds 1, 2, and 3 at the end of the corrosion test. The % protection was determined based on the difference in corrosion rate during the initial baseline measurements (i.e., prior to dosing of inhibitor) and the corrosion rate at the end of the test. The comparative compounds were n-alkyl dimethyl benzyl ammonium chloride, imidazolines, and a polyamide, respectively.

FIG. 2(*b*) is a bar graph depicting % protection of proposed invention 1, 2, 3, and 4 at the end of the corrosion test. The % protection was determined based on the difference in corrosion rate during the initial baseline measurements (i.e., prior to dosing of inhibitor) and the corrosion rate at the end of the test.

DETAILED DESCRIPTION OF THE INVENTION

Figure 1A:
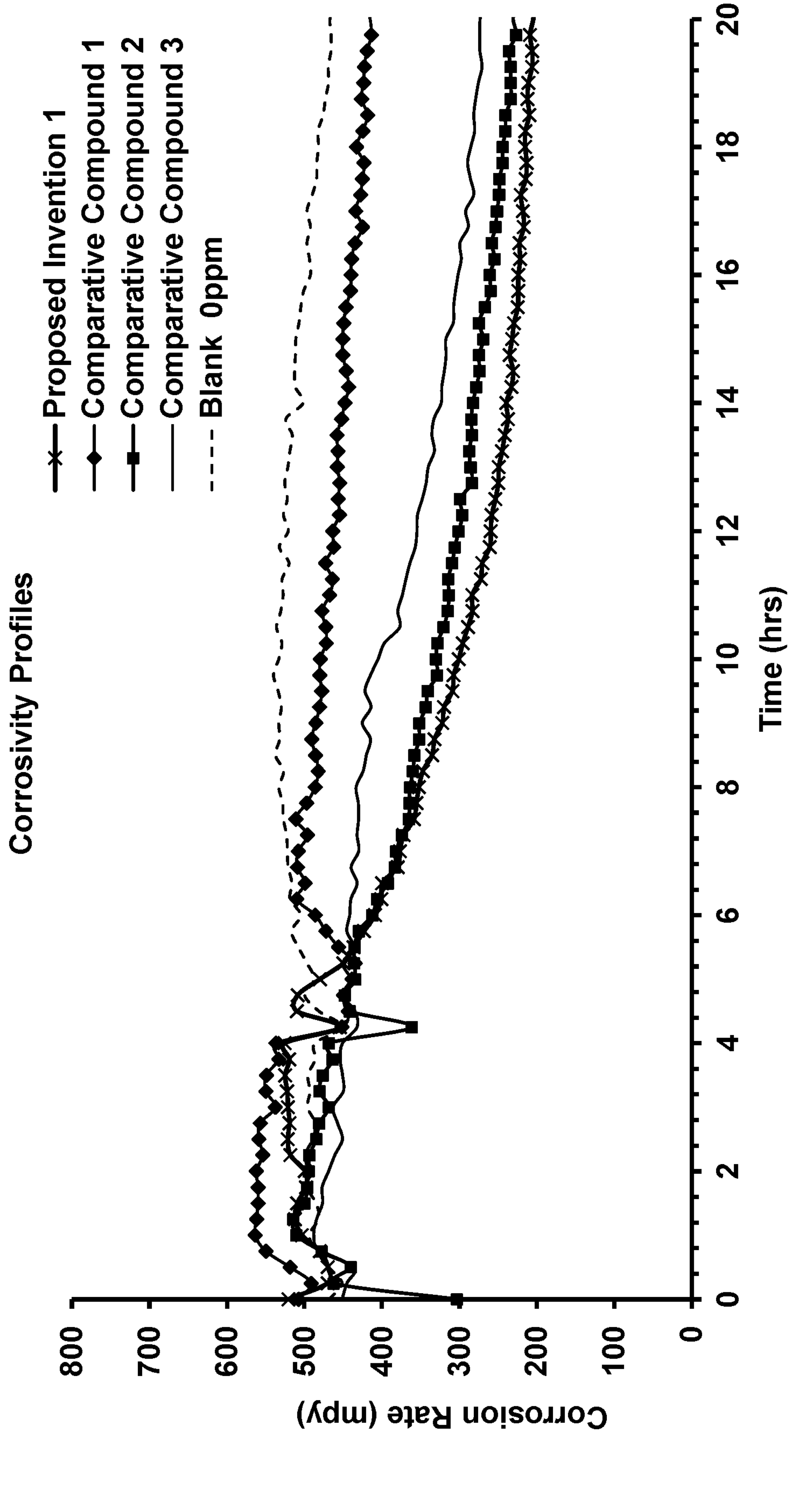
FIG. 1(*a*) is a graph of the corrosion rate versus time showing a corrosivity profile of proposed invention 1 (i.e., Formula 1, $X_1$=C(O)$R_9$ and $R_9$ is $C_{14}$-$C_{18}$ alkyl or alkenyl) and comparative compounds 1, 2, and 3.

Disclosed herein are compounds and compositions, methods of using the compounds and compositions for inhibiting corrosion, and processes for their preparation. The compounds and compositions are useful for inhibiting corrosion in industrial systems. The compositions and methods are particularly useful for inhibiting corrosion in equipment used in the refining of crude oil and natural gas. The compositions include a class of polyamine corrosion inhibitors that are effective and environmentally friendly. These compounds are chloride-free, are more environmentally friendly than conventional quaternary amine corrosion inhibitors, meet regulatory requirements, and are effective corrosion inhibitors in a variety of environments including sweet, sour, and high concentrations of organic acids.

Particularly, the non-cationic and halide free nature of the chemistry described herein, enables their use in recirculating systems such as amine units, as well as in the overheads of crude distillation units (CDU) and Fluid Catalytic Cracking Units (FCCU). The presently disclosed corrosion inhibitor compositions may also have an improved toxicological profile when compared to currently available quaternary ammonium chlorides, such as those used in the oil field industry.

The chemical composition represented in Formula 1 or 2 can be used to inhibit aqueous corrosion. Herein, the composition delivers a passivating layer(s) on the targeted metal surface. The aforementioned layer(s) subsequently precludes corroding species found in an aqueous environment (i.e., ammonium chloride salts and other species) from reaching the metal surface, thus minimizing the formation of iron-based corrosion products and corrosion features. The performance of the composition is evaluated via linear polarization resistance (LPR) measurements (corrosion rate) of coupons in the presence of an aqueous brine solution (i.e., $NH_4^+Cl^-$) as well as through wheel box analyses (percent inhibition).

$$\% \text{ Inhibition} = \frac{X_0 - X_i}{X_0} \times 100\%$$

where, $X_0$ is the weight loss of the coupon without inhibitor and $X_i$ is the weight loss in the presence of the inhibitor.

Disclosed herein are polyamine compounds and their use in methods for inhibiting corrosion at a surface, the polyamine compounds corresponding to the structure of Formula 1 or 2, or a salt thereof:

(1)

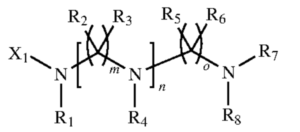

wherein $X_1$ is —$C(O)R_9$ or —$[C(R_{10}R_{11})]_p$—$C(R_{12})(X_2)$—$R_{13}$; $X_2$ is —OH or —$NH_2$; $R_1$ and $R_4$ are independently hydrogen, alkyl, or —$[C(R_{10}R_{11})]_p$—$C(R_{12})(X_2)$—$R_{13}$; $R_2$, $R_3$, $R_5$, $R_6$, $R_7$, $R_8$, $R_{10}$, $R_{11}$, and $R_{12}$ are independently hydrogen or alkyl; $R_9$ and $R_{13}$ are independently $C_7$ to $C_{30}$ alkyl or alkenyl; m and o are integers from 1 to 10; n is an integer from 1 to 6; and p is an integer from 1 to 10;

(2)

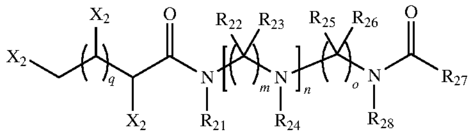

wherein $X_2$ is —OH or —$NH_2$; $R_{21}$, $R_{22}$, $R_{23}$, $R_{24}$, $R_{25}$, $R_{26}$, and $R_{28}$ are independently hydrogen or alkyl; $R_{27}$ is $C_{10}$ to $C_{30}$ alkyl or alkenyl; m and o are integers from 1 to 10; n is an integer from 1 to 6; and q is an integer from 0 to 10.

For the methods described herein, the polyamine compound has a structure of Formula 1.

For the methods, the polyamine compound of Formula 1 has $X_1$ of —$C(O)R_9$.

Alternatively, the polyamine compound of Formula 1 has $X_1$ of —$[C(R_{10}R_{11})]_p$—$C(R_{12})(X_2)$—$R_{13}$.

Additionally, the polyamine compound of Formula 1 has $R_2$, $R_3$, $R_5$, $R_6$, $R_7$, $R_8$, $R_{10}$, $R_{11}$, and $R_{12}$ are independently hydrogen, methyl, or ethyl; preferably, $R_2$, $R_3$, $R_5$, $R_6$, $R_7$, $R_8$, $R_{10}$, $R_{11}$, and $R_{12}$ are hydrogen.

The polyamine compound of Formula 1 can have $R_1$ and $R_4$ independently be hydrogen or —$[C(R_{10}R_{11})]_p$—$C(R_{12})(X_2)$—$R_{13}$.

Additionally, the polyamines of Formula 1 can have $R_9$ and $R_{13}$ independently be $C_7$ to $C_{20}$ alkyl or alkenyl; $C_{11}$ to $C_{18}$ alkyl or alkenyl; or $C_{11}$ to $C_{14}$ alkyl or alkenyl.

For the methods described herein, the polyamine compounds of Formula 1 have $X_2$ of —OH.

For the polyamine compounds of Formula 1, m is an integer from 2 to 6; preferably, m is an integer from 2 to 3; more preferably, m is an integer of 2.

For the polyamine compounds of Formula 1, n is an integer from 2 to 6; preferably, n is an integer from 2 to 5; more preferably, n is an integer of 2 or 3.

The polyamine compounds of Formula 1 also have o as an integer from 2 to 6; preferably, o is an integer from 2 to 3; more preferably, o is an integer of 2.

For the polyamine compounds of Formula 1, p is an integer from 1 to 4; preferably, p is an integer of 1.

The polyamine compounds of Formula 1 can have

For the methods disclosed herein, the polyamine compound has a structure of Formula 2.

For the polyamine compounds of Formula 2, $X_2$ is —OH.

The polyamine compounds of Formula 2 have $R_{21}$, $R_{22}$, $R_{23}$, $R_{24}$, $R_{25}$, $R_{26}$, and $R_{28}$ of independently hydrogen, methyl, or ethyl.

The polyamine compounds of Formula 2 have m of an integer from 2 to 6; preferably, m of an integer of 2 or 3; more preferably, m of an integer of 2.

The polyamine compounds of Formula 2 have n of an integer from 2 to 6; preferably, n of an integer from 2 to 4; more preferably, n of an integer of 2 or 3.

The polyamine compounds of Formula 2 have o of an integer from 2 to 6; preferably, o of an integer of 2 or 3; more preferably, o of an integer of 2.

The polyamine compounds of Formula 2 also have q of an integer from 0 to 6; preferably, q of an integer from 1 to 4; more preferably; q of an integer of 1 or 2; most preferably, q is 0.

For the methods of corrosion inhibition described herein, the polyamine compound of formula 1 or 2 is added to a fluid that contacts the surface.

In these corrosion inhibition methods, the surface is a metal surface.

In the corrosion inhibition methods described herein, the surface is part of a piece of equipment in an oil and gas refinery or petrochemical plant.

In the methods described, the piece of equipment is in a unit susceptible to aqueous corrosion. In particular, the piece of equipment is in an amine unit, a crude distillation unit, or a fluid catalytic cracking unit.

The crude distillation unit is in the first phase of oil refining. The crude distillation unit includes the desalting of the crude oil and the distillation of the crude oil. The desalting process removes impurities from the crude oil before the crude oil is transferred to refining. The desalting process minimizes or eliminates sulfur, water, salts, and mechanical impurities and improves the operation of the pipelines. Additionally, the crude distillation unit includes distillation. The distillation process is characterized by mass-thermal transfer of materials and leads to the obtaining of distillation fractions.

An amine unit provides gas treatment with amine and is also known as amine scrubbing, gas sweetening, or acid gas removal. These processes use aqueous solutions of various amines, typically alkylamines, to remove hydrogen sulfide and carbon dioxide from gases. The amine unit is a common unit process used in crude oil refineries, and it is also used in petrochemical plants, natural gas processing plants, and other industries where removal of acid gases is advantageous.

A fluid catalytic cracking unit (FCCU) converts high boiling point, high molecular weight hydrocarbon fractions of petroleum crude oils into more valuable and lower molecular weight gasoline, olefinic gases, and other products. The catalytic cracking process is advantageous because it produces more gasoline with a higher octane rating and byproduct gases that have more carbon-carbon double bonds than produced using thermal cracking processes. The feedstock for the FCCU is usually crude oil having a boiling point of 340° C. or higher at atmospheric pressure and an average molecular weight ranging from about 200 to 600 or higher and it is often referred to as heavy gas oil or vacuum gas oil (HVGO). In the FCCU, the feedstock is heated to a high temperature and moderate pressure, and contacted with a hot, powdered catalyst. The catalyst helps to break the long chain molecules of the high boiling hydrocarbon liquids into shorter molecules that are collected as a vapor.

The polyamine compound of Formula 1 or 2 forms a film on the surface. Without being bound by theory, the film can form on the surface through chemisorption or physiosorption.

Further, the polyamine compound of Formula 1 or 2 can passivate the surface. Again, without being bound by theory, the polyamine compound can appreciably change the potential of the surface, particularly, a metal surface, usually by forming a protective film on the metal surface.

In the corrosion inhibition methods disclosed, the polyamine compound of Formula 1 or 2 is contacted with the surface at a concentration from 1 ppm to 1000 ppm of the active ingredient based on the refinery stream being treated; preferably, the polyamine compound of Formula 1 or 2 is contacted with the surface at a concentration from 5 ppm to 500 ppm; more preferably, the polyamine compound of Formula 1 or 2 is contacted with the surface at a concentration from 5 ppm to 250 ppm; even more preferably, the polyamine compound of Formula 1 is contacted with the surface at a concentration from 5 ppm to 100 ppm.

For compounds of Formula 1, where $X_1$=C(O)$R_9$, a carboxylic acid, RCOOH, where R can be an alkyl or alkenyl group having 1 to 30 carbon atoms is reacted with a polyamine (e.g., diethylenetriamine, triethylenetetramine, tetraethylenepentamine, and the like) in a suitable solvent at an appropriate temperature until completion of the condensation reaction. Completion of the reaction is determined once consumption of the acid reaches a desired amount.

For compounds of Formula 1, where $X_1$=—$[C(R_{10}R_{11})]_p C(R_{12})(X_2)R_{13}$, an alkyl epoxide, , where R can be an alkyl or alkenyl group having 1 to 30 carbon atoms and preferably 8 to 14 carbon atoms is reacted with the polyamine.

The anti-corrosion compound of Formula 1 or 2 can be contained in an anti-corrosion composition that further comprises one or more additional corrosion inhibitors, an organic solvent, an asphaltene inhibitor, a paraffin inhibitor, a scale inhibitor, an emulsifier, a water clarifier, a dispersant, an emulsion breaker, a gas hydrate inhibitor, a biocide, a pH modifier, a surfactant, or a combination thereof.

The anti-corrosion composition described herein comprises from about 0.1 to about 20 wt. % of one or more compounds of formula 1 or 2 in a solvent system.

The organic solvent can comprise an alcohol, a hydrocarbon, a ketone, an ether, an alkylene glycol, a glycol ether, an amide, a nitrile, a sulfoxide, an ester, or any combination thereof, and the composition optionally comprises water.

Preferably, the organic solvent comprises methanol, ethanol, propanol, isopropanol, butanol, 2-ethylhexanol, hexanol, octanol, decanol, 2-butoxyethanol, methylene glycol, ethylene glycol, 1,2-propylene glycol, 1,3-propylene glycol, diethyleneglycol monomethyl ether, diethylene glycol monoethyl ether, ethylene glycol monobutyl ether, ethylene glycol dibutyl ether, pentane, hexane, cyclohexane, methylcyclohexane, heptane, decane, dodecane, diesel, toluene, xylene, heavy aromatic naphtha, cyclohexanone, diisobutylketone, diethyl ether, propylene carbonate, N-methylpyrrolidinone, N,N-dimethylformamide, or a combination thereof.

A compound used to enhance the corrosion performance of the composition can also be included in the anticorrosion composition. For example, thioglycolic acid, 3,3'-dithiopropioinic acid, thiosulfate, thiourea, 2-mercaptoethanol, L-cysteine, tert-butyl mercaptan, or a combination thereof can be included in the anticorrosion composition.

The methods described herein can have the surface be part of equipment used in an industrial system. Preferably, the industrial system is a water recirculating system, a cooling water system, a boiler water system, a pulp slurry, a papermaking process, a ceramic slurry, a mixed solid/liquid system, or an oil-field system.

The methods described herein can have the fluid be used in the operation of the industrial system.

The fluid can comprise seawater, produced water, fresh water, brackish water, drilling fluid, completion fluid, or a combination thereof.

The compounds/compositions can be used for inhibiting corrosion in oil and gas applications such as by treating a gas or liquid stream with an effective amount of a compound or composition as described herein. The compounds and compositions can be used in any industry where it is desirable to inhibit corrosion at a surface.

The compounds/compositions can be used in water systems, condensate/oil systems/gas systems, or any combination thereof. For example, the compounds/compositions can be used in controlling scale on heat exchanger surfaces.

The compounds/compositions can be applied to a gas or liquid produced, or used in the production, transportation, storage, and/or separation of crude oil or natural gas.

The compounds/compositions can be applied to a gas stream used or produced in a coal-fired process, such as a coal-fired power plant.

The compounds/compositions can be applied to a gas or liquid produced or used in a waste-water process, a farm, a slaughter house, a land-fill, a municipality waste-water plant, a coking coal process, or a biofuel process.

A fluid to which the compounds/compositions can be introduced can be an aqueous medium. The aqueous medium can comprise water, gas, and optionally liquid hydrocarbon.

A fluid to which the compounds/compositions can be introduced can be a liquid hydrocarbon. The liquid hydrocarbon can be any type of liquid hydrocarbon including, but not limited to, crude oil, heavy oil, processed residual oil, bituminous oil, coker oils, coker gas oils, fluid catalytic cracker feeds, gas oil, naphtha, fluid catalytic cracking slurry, diesel fuel, fuel oil, jet fuel, gasoline, and kerosene.

The fluid or gas can be a refined hydrocarbon product.

A fluid or gas treated with a compound/composition can be at any selected temperature, such as ambient temperature or an elevated temperature. The fluid (e.g., liquid hydrocarbon) or gas can be at a temperature of from about 40° C. to about 250° C. The fluid or gas can be at a temperature of from −50° C. to 300° C., 0° C. to 200° C., 10° C. to 100° C., or 20° C. to 90° C. The fluid or gas can be at a temperature of 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., or 40° C. The fluid or gas can be at a temperature of 85° C., 86° C., 87° C., 88° C., 89° C., 90° C., 91° C., 92° C., 93° C., 94° C., 95° C., 96° C., 97° C., 98° C., 99° C., or 100° C.

The compounds/compositions can be added to a fluid at various levels of water cut. For example, the water cut can be from 0% to 100% volume/volume (v/v), from 1% to 80% v/v, or from 1% to 60% v/v. The fluid can be an aqueous medium that contains various levels of salinity. The fluid can have a salinity of 0% to 25%, about 1% to 24%, or about 10% to 25% weight/weight (w/w) total dissolved solids (TDS).

The fluid or gas in which the compounds/compositions are introduced can be contained in and/or exposed to many different types of apparatuses. For example, the fluid or gas can be contained in an apparatus that transports fluid or gas from one point to another, such as an oil and/or gas pipeline. The apparatus can be part of an oil and/or gas refinery, such as a pipeline, a separation vessel, a dehydration unit, or a gas line. The apparatus can be a scrubber (e.g., a wet flue gas desulfurizer, a spray dry absorber, a dry sorbent injector, a spray tower, a contact or bubble tower, or the like). The apparatus can be a cargo vessel, a storage vessel, a holding tank, or a pipeline connecting the tanks, vessels, or processing units.

The compounds/compositions can be introduced into a fluid or gas by any appropriate method for ensuring dispersal through the fluid or gas.

The compounds/compositions can be added to the hydrocarbon fluid before the hydrocarbon fluid contacts the surface.

The compounds/compositions can be added at a point in a flow line upstream from the point at which corrosion prevention is desired.

The compounds/compositions can be injected using mechanical equipment such as chemical injection pumps, piping tees, injection fittings, atomizers, quills, and the like.

The compounds/compositions of the invention can be introduced with or without one or more additional polar or non-polar solvents depending upon the application and requirements.

The compounds/compositions can be pumped into an oil and/or gas pipeline using an umbilical line. A capillary injection system can be used to deliver the compounds/compositions to a selected fluid.

The compounds/compositions can be introduced into a liquid and mixed.

The compounds/compositions can be injected into a gas stream as an aqueous or non-aqueous solution, mixture, or slurry.

The fluid or gas can be passed through an absorption tower comprising compounds/compositions.

The compounds/compositions can be applied continuously, in batch, or a combination thereof. The compounds/compositions doses can be continuous to prevent corrosion. The compounds/compositions doses can be intermittent (i.e., batch treatment) or the compounds/compositions doses can be continuous/maintained and/or intermittent to inhibit corrosion.

The flow rate of a flow line in which the compound/composition is used can be between 0 and 100 feet per second, or between 0.1 and 50 feet per second. The compounds/compositions can also be formulated with water in order to facilitate addition to the flow line.

The compounds/compositions of the invention can be used for inhibiting corrosion in other applications.

The compounds/compositions can also be used on or in other industrial equipment and in other industrial process streams such as heaters, cooling towers, boilers, retort waters, rinse waters, aseptic packaging wash waters, and the like.

The compounds/compositions can be dispensed by immersing either intermittently or continuously in water. The composition can then dissolve, for example, at a controlled or predetermined rate. The rate can be effective to maintain a concentration of dissolved agent that is effective for use according to the methods disclosed herein.

The term "alkyl," as used herein, refers to a linear or branched hydrocarbon radical, preferably having 1 to 32 carbon atoms (i.e., 1, 2, 3, 4, 5, 6, 7, 8, 9, 10, 11, 12, 13, 14, 15, 16, 17, 18, 19, 20, 21, 22, 23, 24, 25, 26, 27, 28, 39, 30, 31, or 32 carbons). Alkyl groups include, but are not limited to, methyl, ethyl, n-propyl, isopropyl, n-butyl, iso-butyl, secondary-butyl, and tertiary-butyl. Alkyl groups may be unsubstituted or substituted by one or more suitable substituents, as defined above.

The term "alkenyl," as used herein, refers to a straight or branched hydrocarbon radical, preferably having 2, 3, 4, 5, 6, 7, 8, 9, 10, 11, 12, 13, 14, 15, 16, 17, 18, 19, 20, 21, 22, 23, 24, 25, 26, 27, 28, 39, 30, 31, or 32 carbons, and having one or more carbon-carbon double bonds. Alkenyl groups include, but are not limited to, ethenyl, 1-propenyl, 2-propenyl (allyl), iso-propenyl, 2-methyl-1-propenyl, 1-butenyl, and 2-butenyl. Alkenyl groups may be unsubstituted or substituted by one or more suitable substituents, as defined above.

The term "alkoxy," as used herein, refers to an alkyl group, as defined herein, appended to the parent molecular moiety through an oxygen atom.

The term "aryl," as used herein, means monocyclic, bicyclic, or tricyclic aromatic radicals such as phenyl, naphthyl, tetrahydronaphthyl, indanyl and the like; optionally substituted by one or more suitable substituents, preferably 1 to 5 suitable substituents, as defined above.

The term "cycloalkyl," as used herein, refers to a mono, bicyclic or tricyclic carbocyclic radical (e.g., cyclopropyl, cyclobutyl, cyclopentyl, cyclohexyl, cycloheptyl, cyclooctyl, cyclononyl, cyclopentenyl, cyclohexenyl, bicyclo[2.2.1]heptanyl, bicyclo[3.2.1]octanyl and bicyclo[5.2.0]nonanyl, etc.); optionally containing 1 or 2 double bonds. Cycloalkyl groups may be unsubstituted or substituted by one or more suitable substituents, preferably 1 to 5 suitable substituents, as defined above.

The term "halo" or "halogen," as used herein, refers to a fluoro, chloro, bromo or iodo radical.

The term "heteroaryl," as used herein, refers to a monocyclic, bicyclic, or tricyclic aromatic heterocyclic group containing one or more heteroatoms (e.g., 1 to 3 heteroatoms) selected from O, S and N in the ring(s). Heteroaryl groups include, but are not limited to, pyridyl, pyrazinyl, pyrimidinyl, pyridazinyl, thienyl, furyl, imidazolyl, pyrrolyl, oxazolyl (e.g., 1,3-oxazolyl, 1,2-oxazolyl), thiazolyl (e.g., 1,2-thiazolyl, 1,3-thiazolyl), pyrazolyl, tetrazolyl, triazolyl (e.g., 1,2,3-triazolyl, 1,2,4-triazolyl), oxadiazolyl (e.g., 1,2,3-oxadiazolyl), thiadiazolyl (e.g., 1,3,4-thiadiazolyl), quinolyl, isoquinolyl, benzothienyl, benzofuryl, and indolyl. Heteroaryl groups may be unsubstituted or substituted by one or more suitable substituents, preferably 1 to 5 suitable substituents, as defined above.

The term "heterocycle" or "heterocyclyl," as used herein, refers to a monocyclic, bicyclic, or tricyclic group containing 1 to 4 heteroatoms selected from N, O, $S(O)_n$, $P(O)_n$, $PR_z$, NH or $NR_z$, wherein $R_z$ is a suitable substituent. Heterocyclic groups optionally contain 1 or 2 double bonds. Heterocyclic groups include, but are not limited to, azetidinyl, tetrahydrofuranyl, imidazolidinyl, pyrrolidinyl, piperidinyl, piperazinyl, oxazolidinyl, thiazolidinyl, pyrazolidinyl, thiomorpholinyl, tetrahydrothiazinyl, tetrahydrothiadiazinyl, morpholinyl, oxetanyl, tetrahydrodiazinyl, oxazinyl, oxathiazinyl, indolinyl, isoindolinyl, quinuclidinyl, chromanyl, isochromanyl, and benzoxazinyl. Examples of monocyclic saturated or partially saturated ring systems are tetrahydrofuran-2-yl, tetrahydrofuran-3-yl, imidazolidin-1-yl, imidazolidin-2-yl, imidazolidin-4-yl, pyrrolidin-1-yl, pyrrolidin-2-yl, pyrrolidin-3-yl, piperidin-1-yl, piperidin-2-yl, piperidin-3-yl, piperazin-1-yl, piperazin-2-yl, piperazin-3-yl, 1,3-oxazolidin-3-yl, isothiazolidine, 1,3-thiazolidin-3-yl, 1,2-pyrazolidin-2-yl, 1,3-pyrazolidin-1-yl, thiomorpholin-yl, 1,2-tetrahydrothiazin-2-yl, 1,3-tetrahydrothiazin-3-yl, tetrahydrothiadiazin-yl, morpholin-yl, 1,2-tetrahydrodiazin-2-yl, 1,3-tetrahydrodiazin-1-yl, 1,4-oxazin-2-yl, and 1,2,5-oxathiazin-4-yl. Heterocyclic groups may be unsubstituted or substituted by one or more suitable substituents, preferably 1 to 3 suitable substituents, as defined above.

The term "hydroxy," as used herein, refers to an —OH group.

The term "suitable substituent," as used herein, is intended to mean a chemically acceptable functional group, preferably a moiety that does not negate the activity of the inventive compounds. Such suitable substituents include, but are not limited to halo groups, perfluoroalkyl groups, perfluoroalkoxy groups, alkyl groups, alkenyl groups, alkynyl groups, hydroxy groups, oxo groups, mercapto groups, alkylthio groups, alkoxy groups, aryl or heteroaryl groups, aryloxy or heteroaryloxy groups, aralkyl or heteroaralkyl groups, aralkoxy or heteroaralkoxy groups, HO—(C═O)— groups, heterocylic groups, cycloalkyl groups, amino groups, alkyl- and dialkylamino groups, carbamoyl groups, alkylcarbonyl groups, alkoxycarbonyl groups, alkylaminocarbonyl groups, dialkylamino carbonyl groups, arylcarbonyl groups, aryloxycarbonyl groups, alkylsulfonyl groups, and arylsulfonyl groups. Those skilled in the art will appreciate that many substituents can be substituted by additional substituents.

The term "water cut," as used herein, means the percentage of water in a composition containing an oil and water mixture.

Having described the invention in detail, it will be apparent that modifications and variations are possible without departing from the scope of the invention defined in the appended claims.

EXAMPLES

The following non-limiting examples are provided to further illustrate the invention.

Example 1: Synthesis of Compounds

For compounds of Formula 1, where $X_1$=C(O)$R_9$, a carboxylic acid, RCOOH, where R can be an alkyl or alkenyl group having 1 to 30 carbon atoms is reacted with a polyamine (e.g., diethylenetriamine, triethylenetetramine, tetraethylenepentamine, and the like) in a suitable solvent at an appropriate temperature until completion of the condensation reaction. Completion of the reaction is determined once consumption of the acid reaches a desired amount.

For compounds of Formula 1, where $X_1$=—[C($R_{10}R_{11}$)]$_p$ C($R_{12}$)($X_2$)$R_{13}$, an alkyl epoxide, r, where R can be an alkyl or alkenyl group having 1 to 30 carbon atoms and preferably 8 to 14 carbon atoms is reacted with the polyamine.

Example 2: Corrosion Testing

The corrosion inhibition ability of the polyamine compounds of Formulae 1 and 2 was evaluated using corrosion rate assessment derived from linear polarization resistance (LPR) analysis as well as wheel box analysis of C1018 carbon steel coupons. Table 1 summarizes the experimental conditions used in the bubble cells to test for aqueous corrosion of C1018 carbon steel metallurgy.

TABLE 1

Summary of Bubble Cell Test Conditions

| Experimental Parameter | Parameter |
|---|---|
| Medium | 1M $NH_4Cl$ |
| Atmosphere | Nitrogen Blanket |
| Stirring | 100 rpm |
| Temperature | 82° C. |
| Inhibitor Dose | 10 ppm |
| MPY Measurement | Electrochemical-Instantaneous (1 point/15 min) |
| Electrodes | Carbon Steel (1018) |

Bubble Cell Test Procedure. The effect of polyamine compounds as corrosion inhibitors was tested using standard bubble cell test procedures. The bubble test simulated low flow areas where little or no mixing of water and oil occurs. The test was conducted using 1 M ammonium chloride ($NH_4Cl$) in water. The ammonium chloride was placed into kettles and purged with nitrogen. The ammonium chloride was continually purged with nitrogen to form a nitrogen blanket prior to starting the test. After the test began, the nitrogen blanketing of the test cell was continued from one hour prior to electrode insertion and through the duration of the test. The kettles were stirred at 100 revolutions per minute (rpm) for the duration of the test to maintain thermal equilibrium at 82° C. The corrosion rate was measured by Linear Polarization Resistance (LPR) techniques. The working electrode used was 1018 carbon steel. The counter and reference electrodes were both Hastelloy. The electrodes were all cleaned with solvent prior to testing. Data were collected for four hours before each of the compositions was dosed into its respective cell. Data were collected overnight.

Figure 1B:
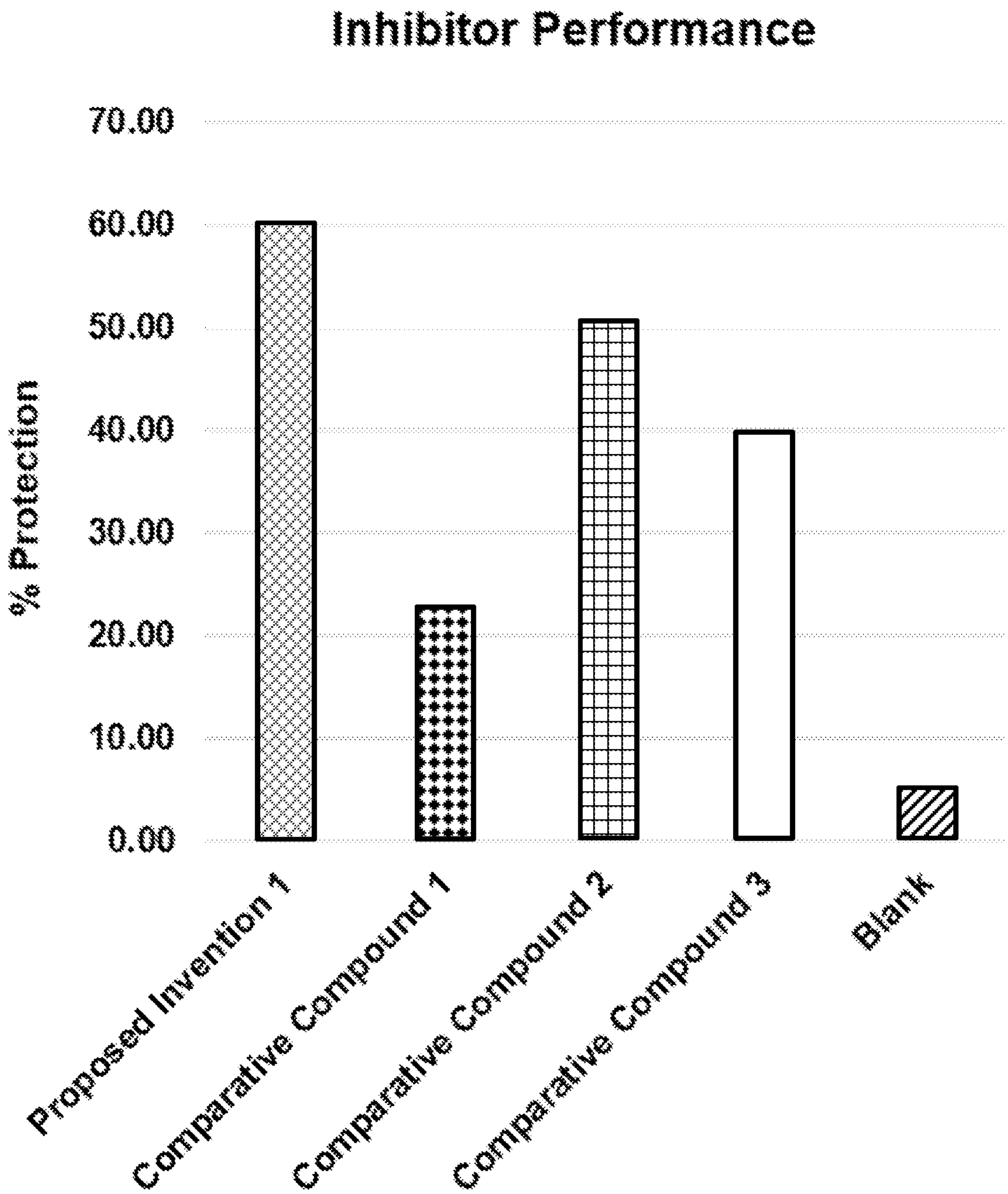
Figure 2A:
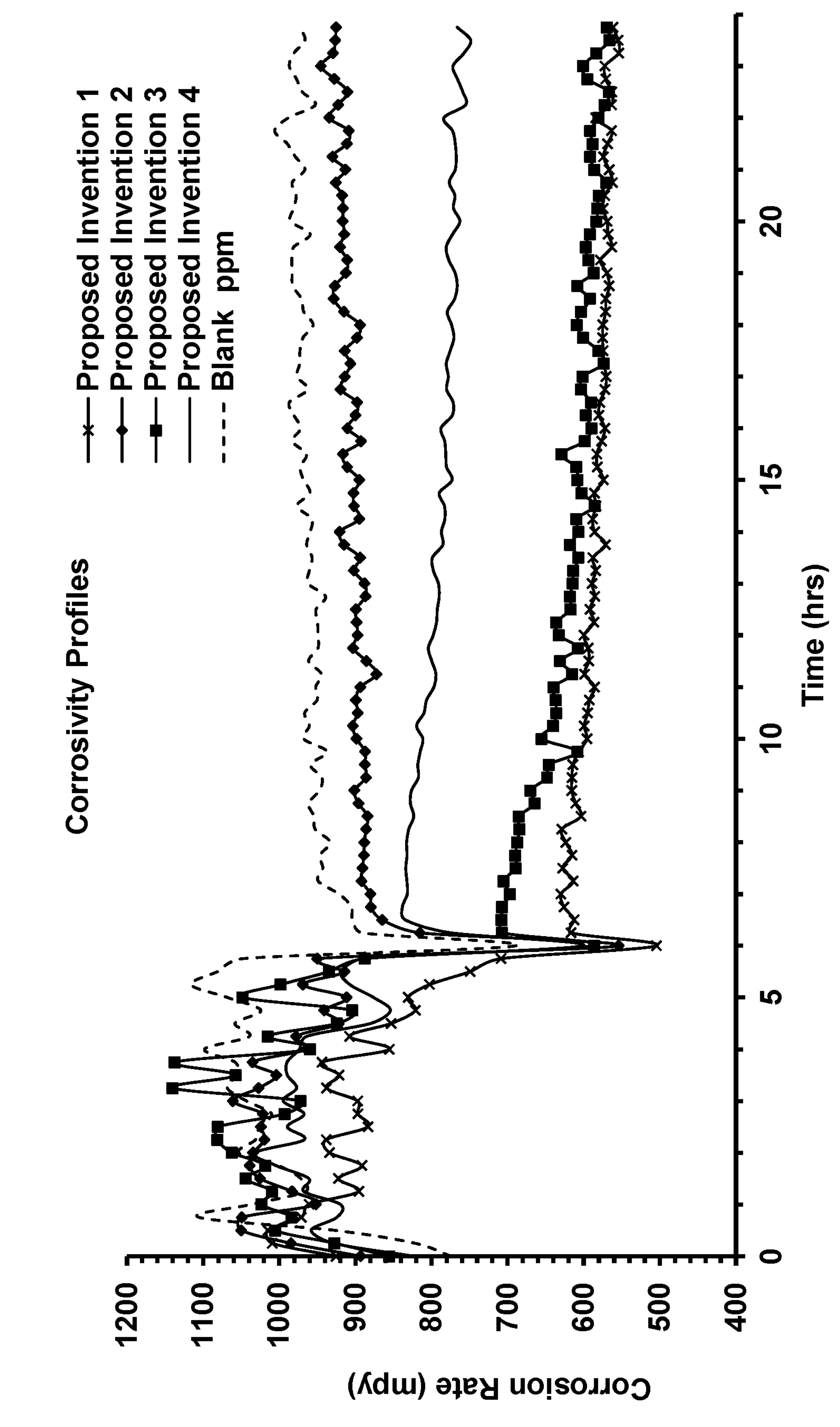
FIG. 2(*a*) is a graph of the corrosion rate versus time shoring a corrosivity profile of proposed invention 1 (i.e., Formula 1, $X_1$=C(O)$R_9$ and $R_9$ is $C_{14}$-$C_{18}$ alkyl or alkenyl), proposed invention 2 (i.e., Formula 1, $X_1$=—[C($R_{10}R_{11}$)]$_p$C($R_{12}$)($X_2$)$R_{13}$; $X_2$ is —OH or —$NH_2$; $R_{13}$=$C_5$-$C_{10}$), proposed invention 3 (i.e., Formula 1, $X_1$=—[C($R_{10}R_{11}$)]$_p$C($R_{12}$)($X_2$)$R_{13}$; $X_2$ is —OH or —$NH_2$, $R_{13}$=$C_{12}$-$C_{14}$), and proposed invention 4 (i.e., Formula 1, $X_1$=—[C($R_{10}R_{11}$)]$_p$C($R_{12}$)($X_2$)$R_{13}$; $X_2$ is —OH or —$NH_2$, $R_{13}$=$C_{12}$-$C_{14}$)).
Figure 2B:
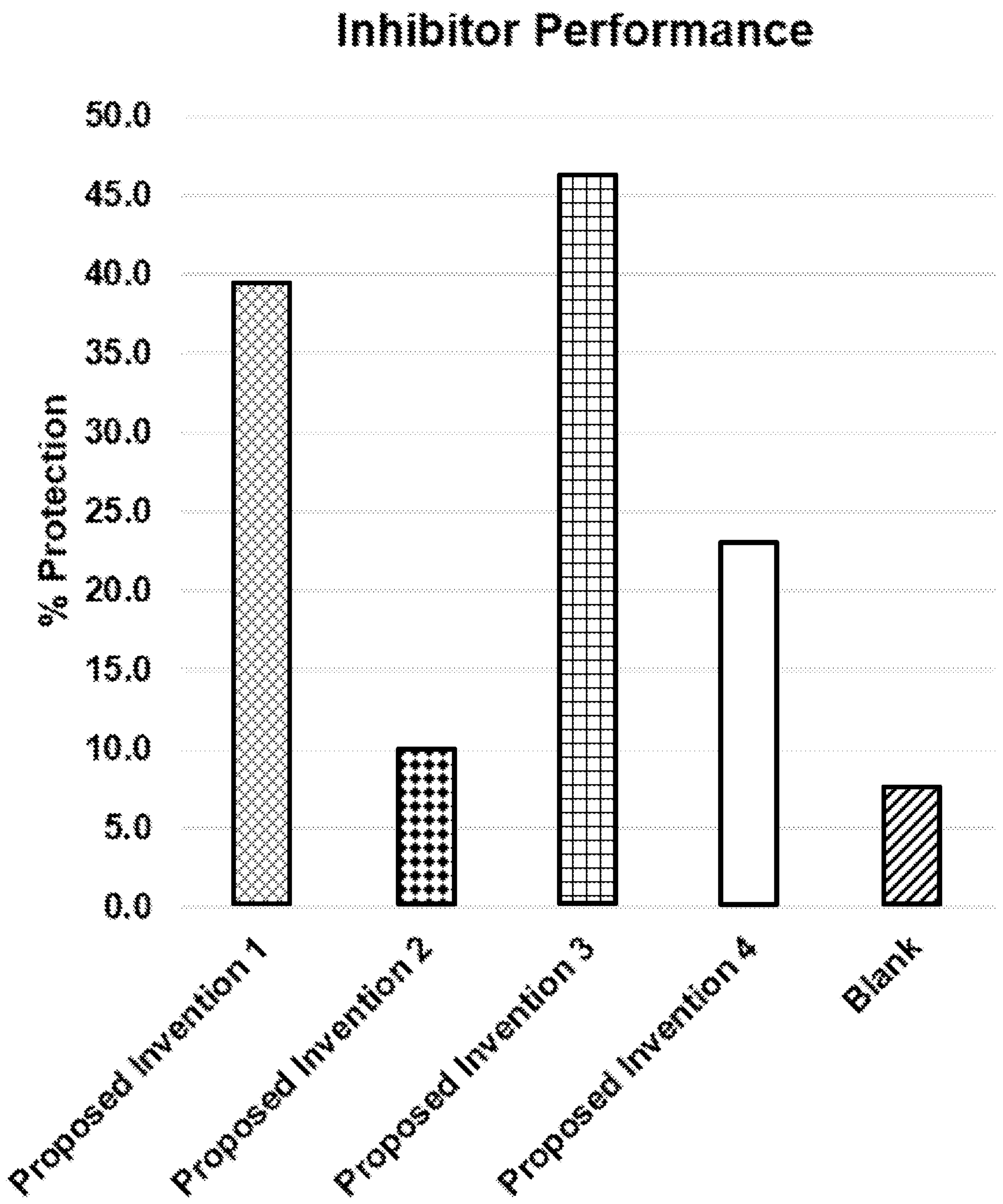

After collecting baseline corrosion rates in ammonium chloride for about 4 hours, the polyamine compounds were dosed into bubble cells at a concentration of 10 ppm. The corrosivity profiles of the polyamine compounds are shown in FIGS. 1 and 2. FIG. 1 shows a comparison of the corrosion rate obtained through LPR analysis of the invention bearing Formula 1 (Proposed Invention 1) to other water-soluble or water dispersible actives as comparator chemistries (e.g., n-alkyl dimethyl benzyl ammonium chloride and a polyamide). Note that the corrosion rate of the C1018 electrodes exhibits a steady decline in the corrosion rate which is not observed with the other tested actives. FIG. 2 shows a comparison of the corrosion rate, obtained through LPR analysis, of the invention bearing Formula 1 where $X_1$ is —C(O)$R_9$ (Proposed Invention 1) to variants of Formula 1 where $X_1$ is —[C($R_{10}R_{11}$)]$_p$—C($R_{12}$)($X_2$)—$R_{13}$ (Proposed inventions 2, 3, and 4). Note that the performance of the polyamine compounds of Formula 1 where $X_1$ is —C(O)$R_9$ is more effective than the polyamines of Formula 1 where $X_1$ is $—[C(R_{10}R_{11})]_p—C(R_{12})(X_2)—R_{13}$, except for where $R_{13}$ is an alkyl chain of 12 to 14 carbons where the efficacy is similar.

The terms "comprise(s)," "include(s)," "having," "has," "can," "contain(s)," and variants thereof, as used herein, are intended to be open-ended transitional phrases, terms, or words that do not preclude the possibility of additional steps or components. The singular forms "a," "and," "the" and "said" include plural references unless the context clearly dictates otherwise. The present disclosure also contemplates other embodiments "comprising," "consisting of" and "consisting essentially of," the embodiments or elements presented herein, whether explicitly set forth or not.

In view of the above, it will be seen that the several objects of the invention are achieved and other advantageous results attained.

As various changes could be made in the above compositions and processes without departing from the scope of the invention, it is intended that all matter contained in the above description shall be interpreted as illustrative and not in a limiting sense.

What is claimed is:

1. A method of inhibiting corrosion at a surface, the method comprising contacting the surface with a corrosion-inhibiting effective amount of a polyamine compound of formula 1, the polyamine compound of formula 1 having the structure:

(1)

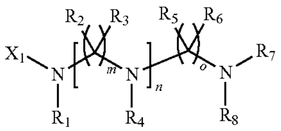

wherein $X_1$ is $—[C(R_{10}R_{11})]_p—C(R_{12})(X_2)—R_{13}$;

$X_2$ is —OH or $—NH_2$;

$R_1$ and $R_4$ are independently hydrogen, alkyl, or $—[C(R_{10}R_{11})]_p—C(R_{12})(X_2)—R_{13}$;

$R_2$, $R_3$, $R_5$, $R_6$, $R_7$, $R_8$, $R_{10}$, $R_{11}$, and $R_{12}$ are independently hydrogen or alkyl;

$R_{13}$ is $C_7$ to $C_{20}$ alkyl or $C_7$ to $C_{20}$ alkenyl;

m and o are integers from 1 to 10;

n is an integer from 1 to 6; and p is an integer from 1 to 10.

2. The method of claim 1, wherein $R_1$ and $R_4$ are independently hydrogen or $—[C(R_{10}R_{11})]_p—C(R_{12})(X_2)—R_{13}$.

3. The method of claim 2, wherein $R_2$, $R_3$, $R_5$, $R_6$, $R_7$, $R_8$, $R_{10}$, $R_{11}$, and $R_{12}$ are independently hydrogen, methyl, or ethyl.

4. The method of claim 2, wherein $X_2$ is —OH.

5. The method of claim 1, wherein m is an integer from 2 to 6.

6. The method of claim 5, wherein n is an integer from 2 to 6.

7. The method of claim 6, wherein o is an integer from 2 to 6.

8. The method of claim 7, wherein p is an integer from 1 to 4.

9. A method of inhibiting corrosion at a surface, the method comprising contacting the surface with a corrosion-inhibiting effective amount of a polyamine compound having a structure of Formula 2

(2)

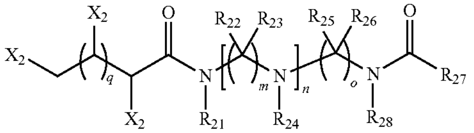

wherein $X_2$ is —OH or $—NH_2$;

$R_{21}$, $R_{22}$, $R_{23}$, $R_{24}$, $R_{25}$, $R_{26}$, and $R_{28}$ are independently hydrogen or alkyl;

$R_{27}$ is $C_{10}$ to $C_{30}$ alkyl or $C_{10}$ to $C_{30}$ alkenyl;

m and o are integers from 1 to 10;

n is an integer from 1 to 6; and q is an integer from 0 to 10.

10. The method of claim 9, wherein $X_2$ is —OH.

11. The method of claim 10, wherein $R_{21}$, $R_{22}$, $R_{23}$, $R_{24}$, $R_{25}$, $R_{26}$, and $R_{28}$ are independently hydrogen, methyl, or ethyl.

12. The method of claim 10, wherein m is an integer from 2 to 6.

13. The method of claim 10, wherein n is an integer from 2 to 6.

14. The method of claim 10, wherein o is an integer from 2 to 6 and q is an integer from 0 to 6.

15. The method of claim 1, wherein the surface is a metal surface and the surface is part of a piece of equipment in an oil and gas refinery or petroleum plant and the piece of equipment is in a unit susceptible to aqueous corrosion and the piece of equipment is in an amine unit, a crude distillation unit, or a fluid catalytic cracking unit.

16. The method of claim 1, wherein the polyamine compound of Formula 1 is contacted with the surface at a concentration from 1 ppm to 1000 ppm of the active ingredient based on the weight of refinery stream being treated.

17. The method of claim 1, wherein $X_2$ is —OH and $R_{10}$, $R_{11}$, and $R_{12}$ are hydrogen.

* * * * *